United States Patent [19]
Shu et al.

[11] Patent Number: 5,614,392
[45] Date of Patent: Mar. 25, 1997

[54] PROCESS OF L-PHENYLALANINE FERMENTATION

[75] Inventors: Chin-Hang Shu; Chuen-Yang Yeh, both of Hsin Chu Hsien; Pei-Ming Wang, Kao Hsiung; Chii-Cherng Liao, Hsin Chu, all of Taiwan

[73] Assignee: Food Industry Research and Development Institute, Taiwan

[21] Appl. No.: 457,488

[22] Filed: Jun. 1, 1995

[51] Int. Cl.$^6$ .................................................. C12P 13/22
[52] U.S. Cl. .......................................... 435/108; 435/843
[58] Field of Search ...................................... 435/108, 843

[56] References Cited

U.S. PATENT DOCUMENTS

| | | | |
|---|---|---|---|
| 4,681,852 | 7/1987 | Tribe | 435/108 |
| 4,743,547 | 5/1988 | Kitamura et al. | 435/108 |
| 4,755,466 | 7/1988 | Yokozeki et al. | 435/108 |
| 4,900,669 | 2/1990 | Hatch et al. | 435/108 |

OTHER PUBLICATIONS

Derwent Abs. 87–321672/46 Kludas et al. DD–247231 (Jul. 1987).
Derwent Abs. 75–71529W/43 Ajinomoto KK (J50064485)(May. 1975).
Biotech Abs. 91–10001 Konstantinov et al. "J. Ferment Bioeng" (1991) 71, 5, 350–55.
Biotech Abs. 94–15470 "Biotech Tech." (1994) 8, 11, pp. 843–846.

*Primary Examiner*—Herbert J. Lilling
*Attorney, Agent, or Firm*—Bacon & Thomas

[57] ABSTRACT

The present invention provides a process for L-phenylalanine fermentation by coryneform bacterium. The present invention successfully applies an oxystat to control the timing of feeding of molasses so as to maintain low dissolved oxygen tension and low substrate concentrations during the course of fermentation. The oxystat improves fermentation productivity appreciably. Furthermore, the present invention discovers that the proper increases of the oxygen supply rate to the culture decreases product feedback inhibition of phenylalanine formation as phenylalanine concentration increases.

3 Claims, 7 Drawing Sheets

PROCESS OF L-PHENYLALANINE FERMENTATION

FIELD OF THE INVENTION

The present invention relates to process development of L-phenylalanine fermentation by coryneform bacterium. In particular, the present invention relates to process of nutrient feeding strategies for phenylalanine fermentation to maintain low dissolved oxygen tension and low substrate concentrations, and to process of controlling oxygen supply rates, in order to increase phenylalanine productivity.

BACKGROUND OF THE INVENTION

The L-phenylalanine is an essential amino acid for humans and a raw material for production of aspartame, an artificial sweeter. The main industrial processes for phenylalanine production are enzymatic conversions and microbial fermentations. Because it is difficult to get the raw material for the enzymatic conversion, and the cost of the raw material changes significantly from time to time. Thus, the industries prefer to utilize microbial fermentations for phenylalanine production. Fed-batch operation is the most popular fermentation process, since it gives higher productivity than batch fermentationidoes, and it can also get rid of the high contamination problem of the continuous culture. However, as phenylalanine fermentation (see the work of Wang P.-M. et al, 1994, Biotechnology Techniques, V. 8 No. 11, November) was carried out by *Corynebacterium qlutamicum*, the product feedback inhibition by phenylalanine is still present. Besides, no work has mentioned the influence of oxygen supply rate on the product feedback inhibition of phenylalanine formation. The present inventions designs experiments to study the effect of oxygen supply rate on product feedback inhibition, and provides process control methods to decreases product feedback inhibition by proper increases of oxygen supply.

Some previous work in literature used phenylalanine resistant analogues such as phenylalanine p-fluorophenylalanine (p-FP), m-resistant fluorophenylalanine (m-FP), or aromtic amine analogues such as 3-amino-L-tyrosin (3AT), 5-methyltyryptophan (5MT) to screen high phenylalanine producing strains. The screened strains possess higher phenylalanine resistant capability, but phenylalanine production by the screened strains were still inhibited by high phenylalanine concentrations.

Some research work related to the recovery of phenylalanine from fermentation broth in past, such as using copper ions to bind phenylalanine to precipitate out of the solution, or using resin to absorb phenylalanine. But the conditions favoring recovery process do not favor fermentation process. Thus, the current technology still can not provide an economical process to recover phenylalanine from culture.

Thus, product feedback inhibition by phenylalanine is the problem of phenylalanine fermentation, which was alleviated by the present invention increasing oxygen supply rate during the course of fermentation.

Among the methods of controlling substrate feeding policy, the oxystat is an economical, automatic addition method. The oxystat is defined as feeding a limiting substrate only when dissolved oxygen tension increases due to substrate depletion (see the work of Yano T. et al., 1978, J. Ferment. Technol. 56, 416–420). Previous research pointed out that this method can effectively determine the timing of feeding substrate to maintain substrate concentration under low levels, which avoids inhibition of cell growth by high substrate concentrations. This method can also maintain culture under low dissolved oxygen tension. The oxystat has been used in phenylalanine production by recombinant *Escherichia coli* as well. However the final phenylalanine concentration was low due to the production of excess acetic acid under low oxygen tension which inhibited growth (Konstantinov K. et al., 1990, Biotechnol. Bioeng. 36, 750–758). Up to now, no successful attempts using an oxystat for a fed-batch phenylalanine fermentazion have been reported. This is also the problem in prior art of phenylalanine fermentation. The present invention solves this problem by successfully aplying an oxystat to phenylalanine fermentation by coryneform bacterium without production of inhibitory metabolites under low dissolved oxygen tension.

The information about phenylalanine production in literature is limited. As to the correlation between oxygen supply rate and phenylalanine production, it is an accepted concept that phenylalanine formation is favorable under low dissolved oxygen tension. Based on this concept, previous work reported in literature adopted the strategy of controlling culture under a lower oxygen supply rate or under a constant oxygen supply rate in the latter stages of phenylalanine fermentation in order to increase phenylalanine production. However, such strategy neglects the product feedback inhibition by high phenylalnine concentration. On the other hand, as opposite to the prior concept about the strategy of controlling the oxygen supply rate, the present invention provide methods to increase the oxygen supply rate at proper timing to increase fermentation productivity. Since product feedback inhibition is decreased by such process control method.

Thus, in order to improve phenylalanine fermentation productivity, the present invention provides methods to decrease product feedback inhibition by phenylalanine, and to keep culture under low dissolved oxygen tension without producing inhibitory metabolites and to keep substrate under low levels to avoid substrate inhibition on cell growth.

SUMMARY OF THE INVENTION

The present invention solves the problems, production of inhibitory metabolites and present of product feedback inhibition by high L-phenylalanine concentrations, which occurred during development of phenylalanine fermentation process by discovering and inventing an economical process for industrial production. The present invention discovers that the proper increase of oxygen supply rate causes the product feedback inhibition by phenylalanine to be decreased, without affecting the nature of the profiles of dissolved oxygen tension. Thus, the fermentation time can be decreased a lot to achieve a target concentration, and fermentation productivity is improved. In addition, the present invention used coryneform bacterium, preferably *Corynebacterium glutamicum*, as the production organism of phenylalanine fermentation. As an oxystat method was applied for the fed-batch fermentation, there was no production of inhibitory metabolites for the culture under low dissolved oxygen tension. However, as an oxystat was applied to phenylalanine fermentation by *Escherichia coli,* there was an excess production of acetic acid which inhibited cell growth. Furthermore, the present invention uses an oxystat to maintain low substrate concentrations to avoid substrate inhibition during the course of fed-batch fermentation. Moreover, molasses can be chosen as the feeding substrate. Therefore, the present invention provides a process to improve productivity of L-phenylalanine fermentation.

DETAILED DESCRIPTION OF PREFERRED EMBODIMENTS

The present invention used *Corynebacterium glutamicum* CCRC 18335, a mutant of coryneform bacterium, as the production strain of L-phenylalanine fermentation. *Corynebacterium glutamicum* CCRC 18335, was deposited in the American Type Culture Collection (12301 Parklawn Drive, Rockville, Md. 20852) on May 7, 1996, under the terms of the Budapest Treaty and has been designated accession No. 55766. No work has mentioned the influence of oxygen supply rate on the product feedback inhibition of phenylalanine formation. Thus, the present invention used fed-batch fermentation experiments to study effect of product feedback inhibition over a range of oxygen supply rates and a range of initial phenylalanine concentrations. Since the phenylalanine concentration increases along the course of fermentation, the high phenylalanine concentration inhibits product formation of the production organism.

The experiments were carried out in a 5 L agitated fermentor at 30° C. Three liter fermentation medium was used in each run, and the composition (w/v) was 10% molasses (nutrient), 0.3% ammonium sulfate, 0.1% $KH_2PO_4$, 0.1% $K_2HPO_4$, 0.03% $MgSO_4$–$7H_2O$. Five initial phenylalanine concentrations were used in a series of experiments, i.e., 0%, 0.5%, 1.0%, 1.5%, 2.0%. For one initial phenylalanine concentration, three different agitation rates of 400, 600, and 900 rpm were chosen for three different runs respectively, for the mixer of the fermentor for studies of the influence of oxygen supply rate on product feedback inhibition with a constant air flow rate of 1.0 L/min. The pH was controlled at 7.0 with addition of 11.1M $NH_4OH$. Foaming was prevented by the addition of 10% (w/v) Silicone KM-72. The dissolved Oxygen (DO) concentration was measured by a Ingold DO probe. The inoculum was 5%, the culture reviving time was 18–20 hours.

The sampling time was four hours, phenylalanine assayed by HPLC, reducing sugar assayed by dinitrosalicylic acid method. The optical density of the culture was measured at 660 nm to determine the cell concentration. The specific growth rate ($\mu$) was calculated for each fermentation run based on the measurements of the cell concentration.

Figure 1:
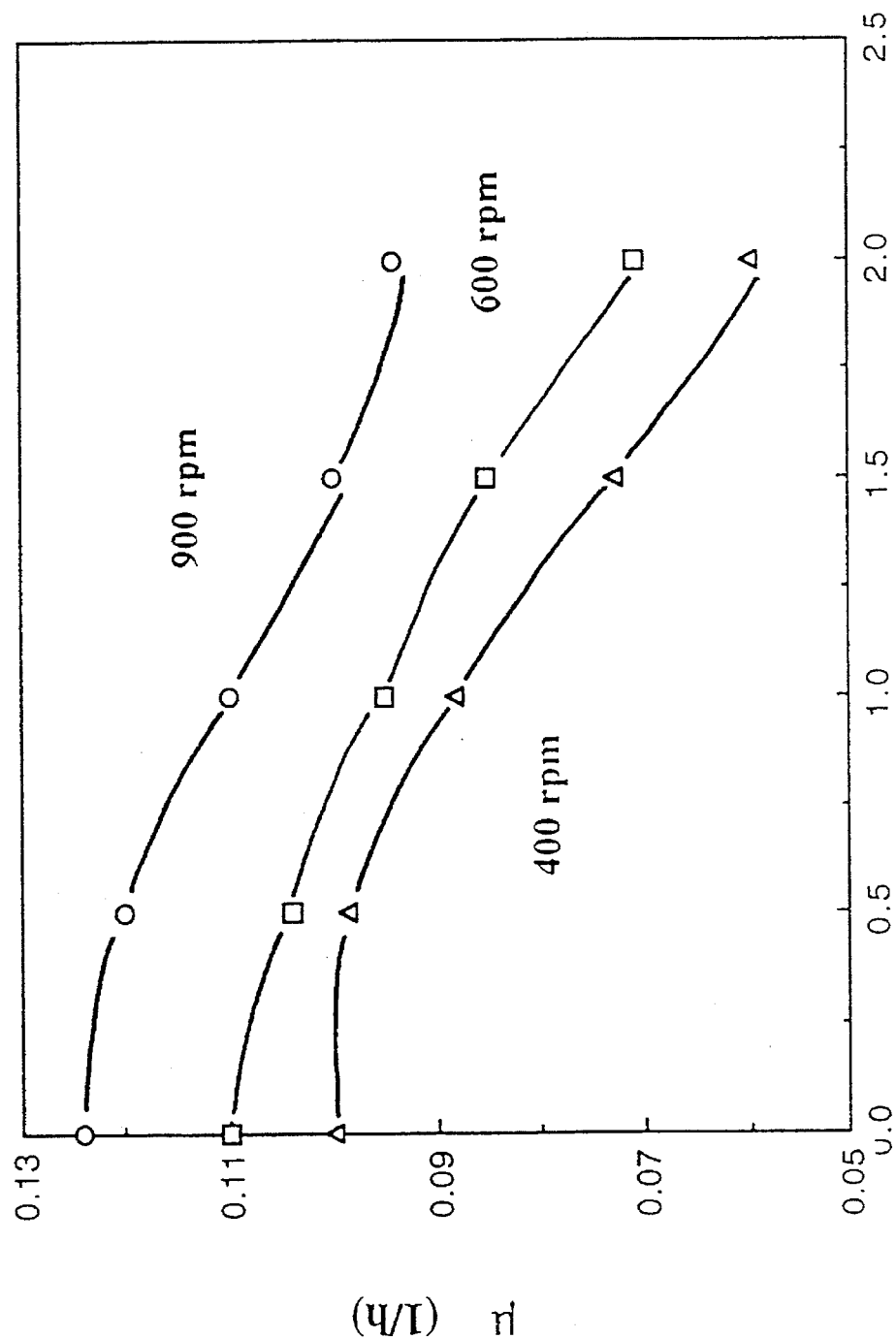
FIG. 1 Effect of the initial phenylalanine concentration on the specific growth rate of *C. glutamicum* under different oxygen supply rates.

Plotting specific growth rate vs. initial phenylalanine concentration shows the correlation of these two variables (FIG. 1). FIG. 1 shows that take change of specific cell growth rate is more dramatic as the initial phenylalanine concentration is higher. Comparing the experimental results for the runs of different oxygen supply rates (different agitation rates) with the same initial phenylalanine concentration, cell grows faster under higher oxygen supply rates.

Figure 2:
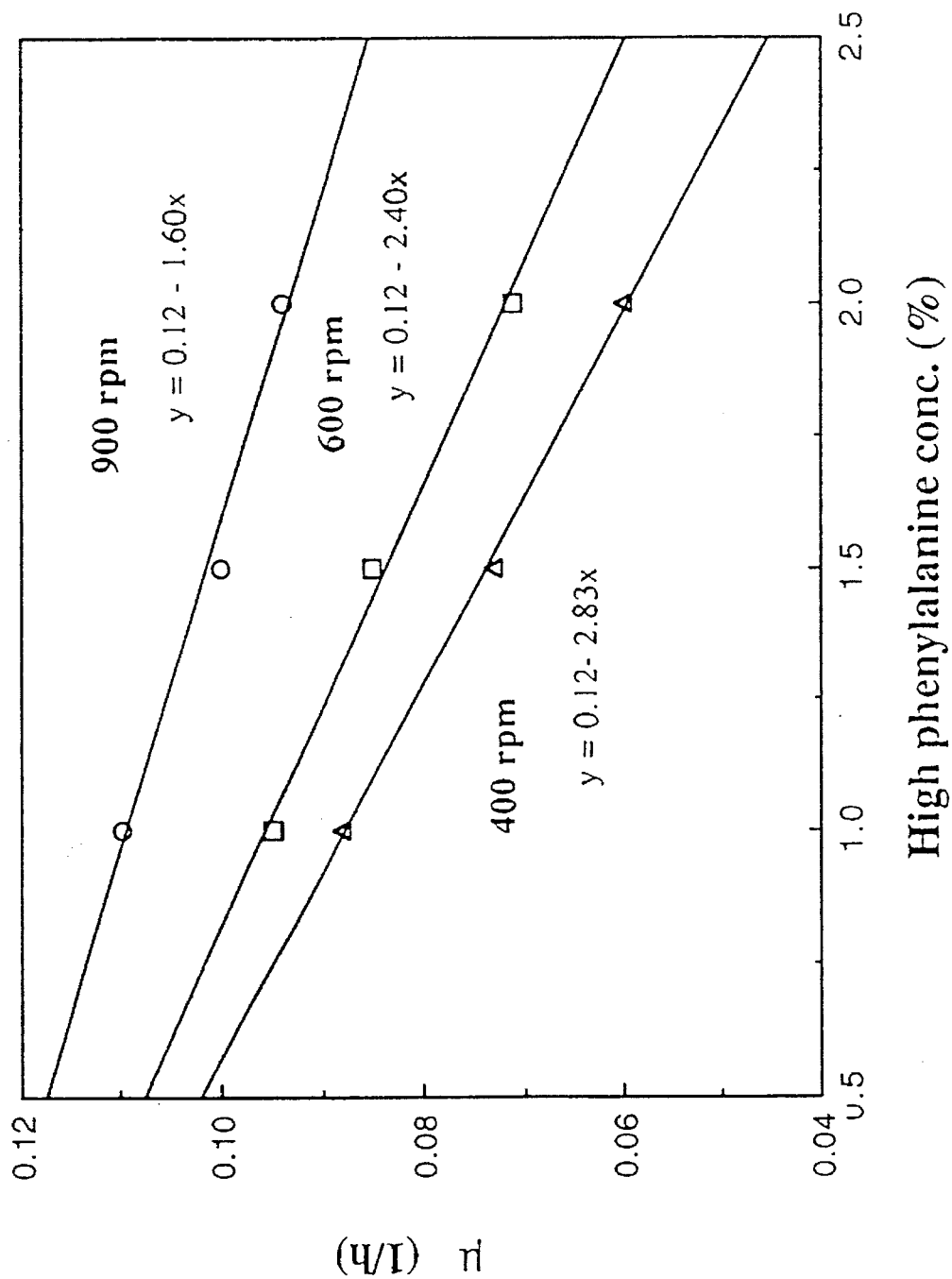
FIG. 2 Extent of product feedback inhibition of cell growth of *C. glutamicum* at high phenylalanine concentrations under different oxygen supply rate.

Let us consider the runt with higher initial phenylalanine concentrations, i.e., which are greater than 1%. When the specific growth rate was plotted against the initial phenylalanine concentration for these runs, we could see the plot shown in FIG. 2. It showed substantial linear correlation for the runs under each oxygen supply rate. From FIG. 2, we could calculate the effect of product feedback inhibition by phenylalanine under each oxygen supply rate. The effect could be defined by the slope of each regression line shown in FIG. 2. The values of the slopes were –1.6, –2.4, –2.83 corresponding to the runs with an oxygen supply rate of 900, 600, 400 rpm, respectively. Thus, we could see that the product feedback inhibition effect decreases as the oxygen supply rate increases. Namely, we could increase oxygen supply rate to the culture to decrease product feedback inhibition by phenylalanine.

Figure 3:
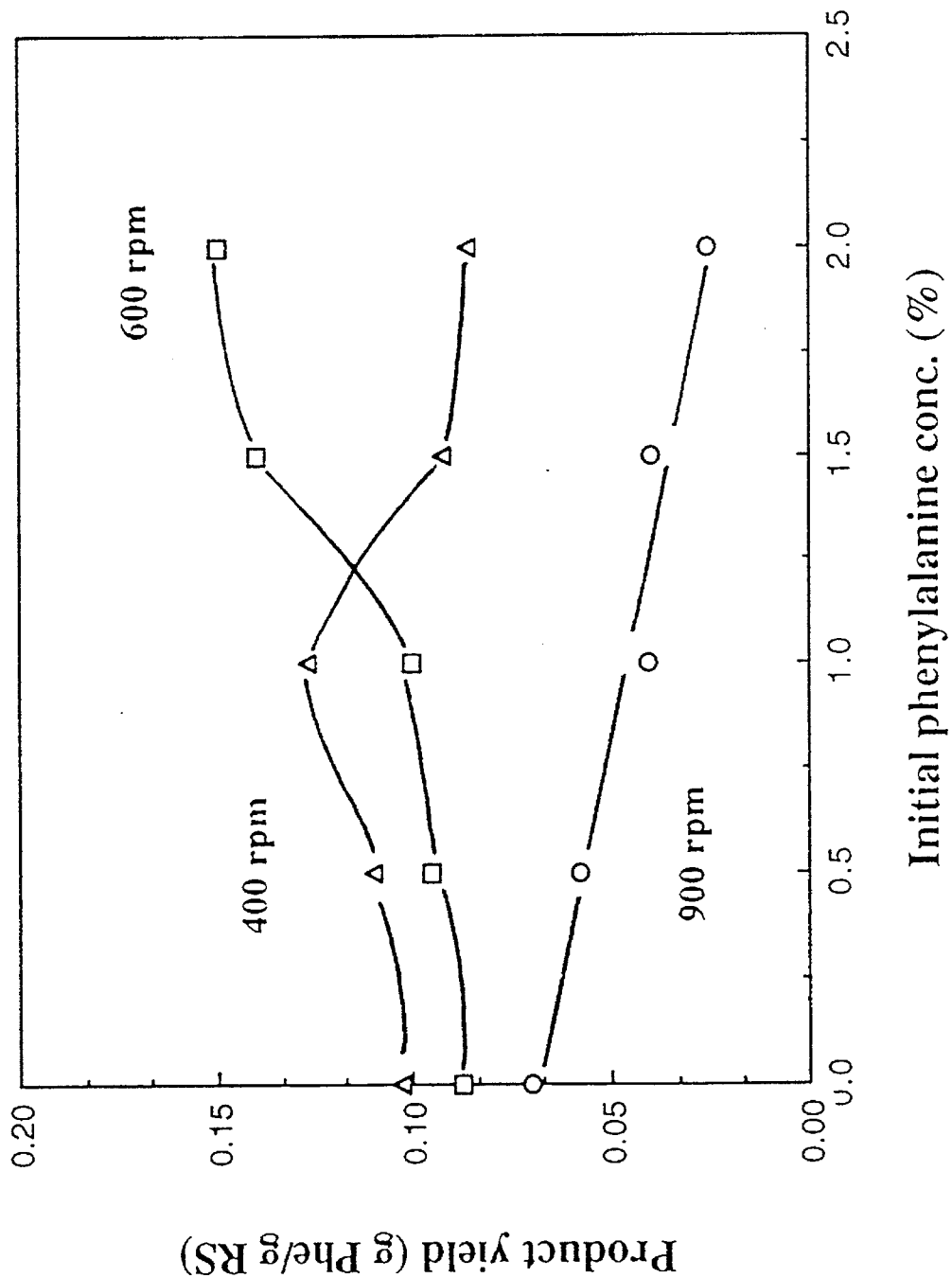
FIG. 3 Effect of the initial phenylalanine concentration on product yield of phenylalanine fermentation under different oxygen supply rates.

For the runs under different oxygen supply rates, the correlation between product yield and initial phenylalanine concentration is shown in FIG. 3. The figure shows that the product yield of the run under 900 rpm is smallest. In addition, for the run under high phenylalanine concentrations, the product yield of the run under 600 rpm is maximum. Therefore, proper increase of oxygen supply rate decreases product feedback inhibition effect and increases fermentation productivity.

The practice of the invention is further illustrated in the examples which follow.

EXAMPLE 1

Culture Reviving and Preservation

*Corynebacterium glutamicum* CCRC 18335 was cultivated in a complete medium. The composition of the medium was (g/L): glucose, 10; sodium chloride, 2.5; yeast extract, 10; peptone, 10. The culture could be maintained in a freezer at 4° C. for 1–2 weeks, or in a complete medium containing 10% glycerol. Freeze culture at –80° C. for preservation in a bottle. Prepare a series of bottles, revive one bottle each month on agar plates of complete medium.

EXAMPLE 2

Fermentation in a 5 L agitated Fermentor

The *C. glutamicum* CCRC 18335 was grown in a liquid complete medium at 30° C. shake flask for 24 hours. The 2.5% seed culture was inoculated to a flask containing seed medium at 30° C., with shaker speed of 150 rpm, for 18–20 hours. The seed medium comprised molasses (w/v), 3.5%; ammonium sulfate 0.3%; soy proteins (hydrolysis from chloric acid), 5%; $K_2HPO_4$, 0.1%; $KH_2PO_4$, 0.01%; $MgSO_{4-7}H_2O$, 0.03%; calcium carbonate, 2%. The pH of the seed medium was 7. Then 6.7% seed culture was transferred to the 5 L fermentor containing 3 L fermentation medium. The temperature of the fermentor was controlled between 30° and 35° C., pH was controlled between 6.8 and 7.5 with the addition of 11.1M $NH_4OH$. The agitation speed of the mixer was 400, or 600, or 900 rpm. The air flow rate was 1.0 L/min. The fermentor was operated in a batch mode.

As to the fed-batch fermentation, 14% seed culture was transferred into 5 L fermentor containing 1.4 L fermentation medium. The agitation speed was 600 rpm, the air flow rate was 1.0 L/min. The temperature and pH controls were the same as those of batch fermentations. The feeding of the nutrient, comprising 50% molasses, started at the second day of the inoculation of the fermentor.

The fermentation medium of the batch and fed-batch operation both comprised molasses (w/v), 7%; ammonium sulfate 0.3%; $K_2HPO_4$, 0.1%; $KH_2O_4$, 0.1%; $MgSO_4\cdot 7H_2O$, 0.03%. The pH of the medium was 7.

EXAMPLE 3

Applying An Oxystat to L-phenylalanine Fermentation

When an oxystat was applied to control the fed-batch fermentation, essentially the fermentor comprised the following apparatus: (a) the dissolve oxygen (DO) electrode and the corresponding display; (b) the computer for data acquisition and the digital controller; (c) the electrically powered pump.

Figure 4A:
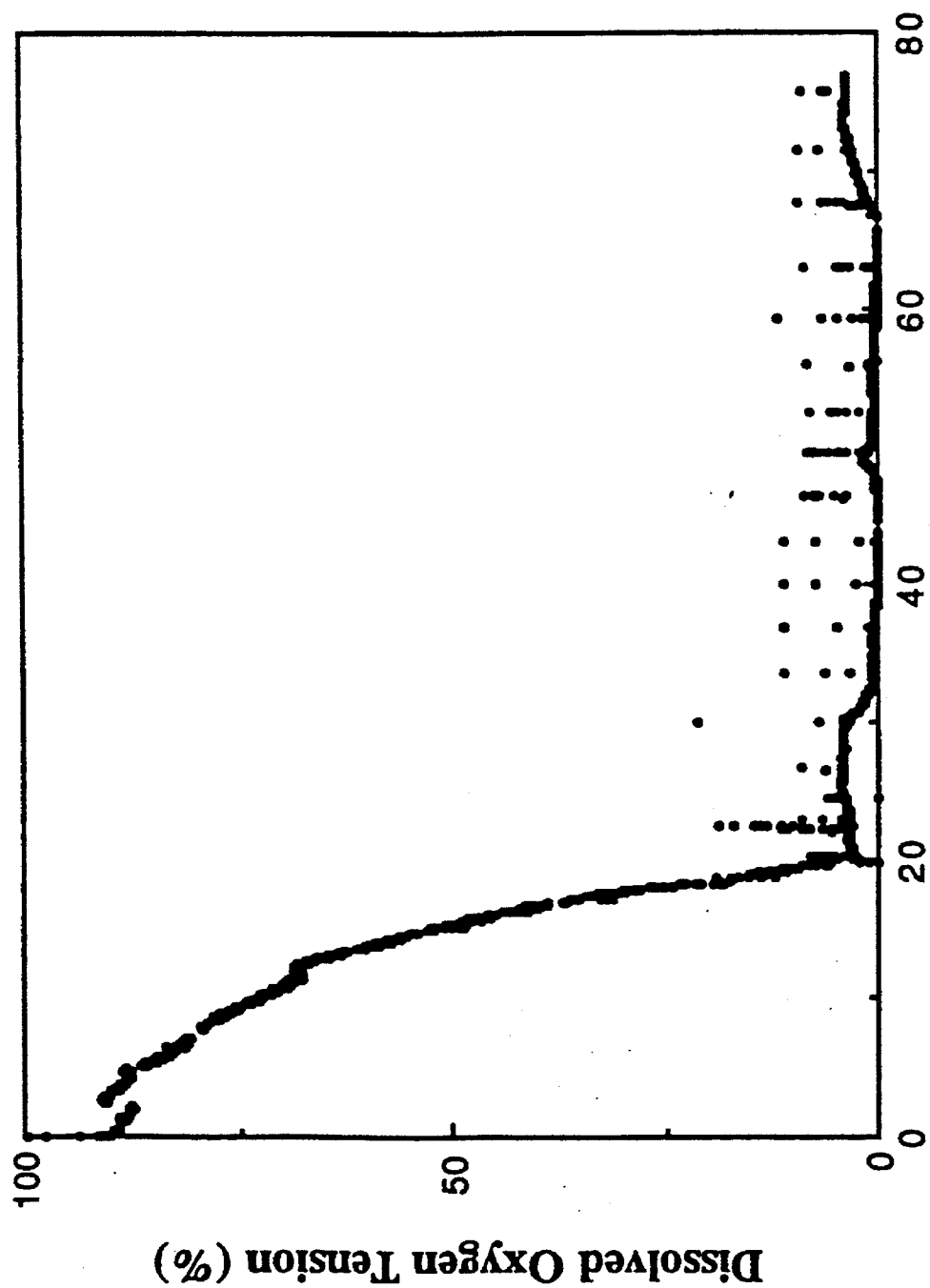
FIGS. 4A–4B Typical time-course data of a fed-batch culture using an oxystat.
Figure 4B:
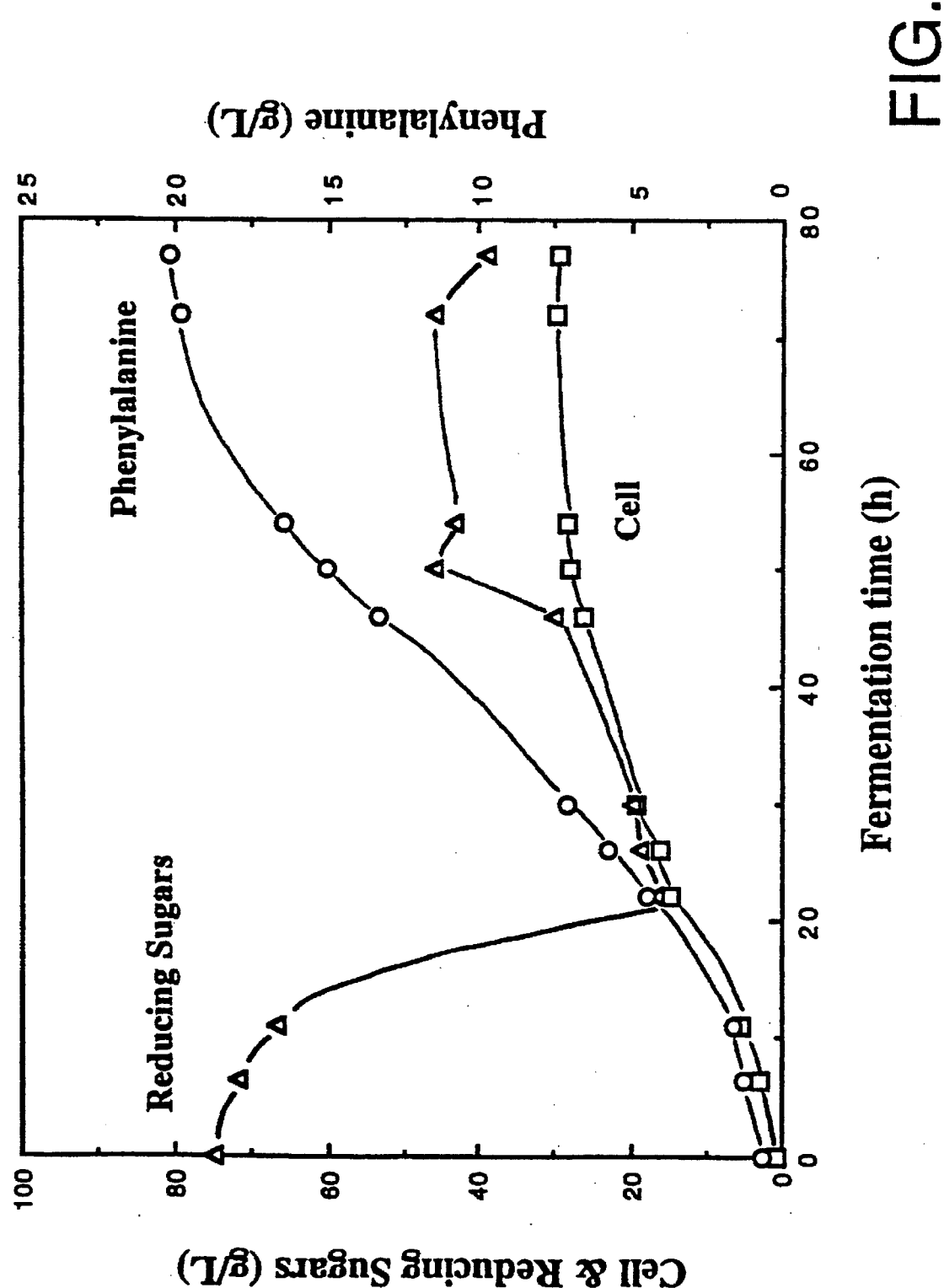

During the early 20–26 hours the fermentation, the operation was mostly in a batch mode. The oxygen supply was controlled at a steady state, i.e., air flow rate, 1 L/min; agitation speed of the mixer, 600 rpm. When the fermentation time was close to 20–26 hours, the DO was maintained around zero until the fermentable sugar was almost depleted. Then DO increased rapidly, and the signal of change of DO from around zero to a appreciable value was received by the computer. Next, the computer sent a signal to power the pump to feed molasses to the fermentor. The feeding rate was set to about 60–80 ml/min for every fixed interval for each input. As molasses was fed into the fermentor, the DO dropped around zero. Repeat this feeding mode over and over until the end of the fermentation. A typical experimental data of an oxystat fed-batch fermentation was shown in FIGS. 4A–4B.

EXAMPLE 4

Influence of Increasing Oxygen Supply Rate on a Fed-Batch L-Phenylalanine Fermentation Increasing oxygen supply rate to the culture would decrease product feedback inhibition of phenylalanine, and would improve fermentation productivity. In order to compare with the results of example 3, the operation conditions were the same as those of example 3 except that at the times of 21.1 and 44 hours, respectively. At the 21st hour, the agitation speed of the mixer was switched from 600 to 900 rpm. At the 44th hour, the air flow rate was switched from 1.0 to 2.0 L/min. We discovered that the productivity of phenylalanine fermentation increased as shown in FIGS. 5A–5b.

Figure 5A:
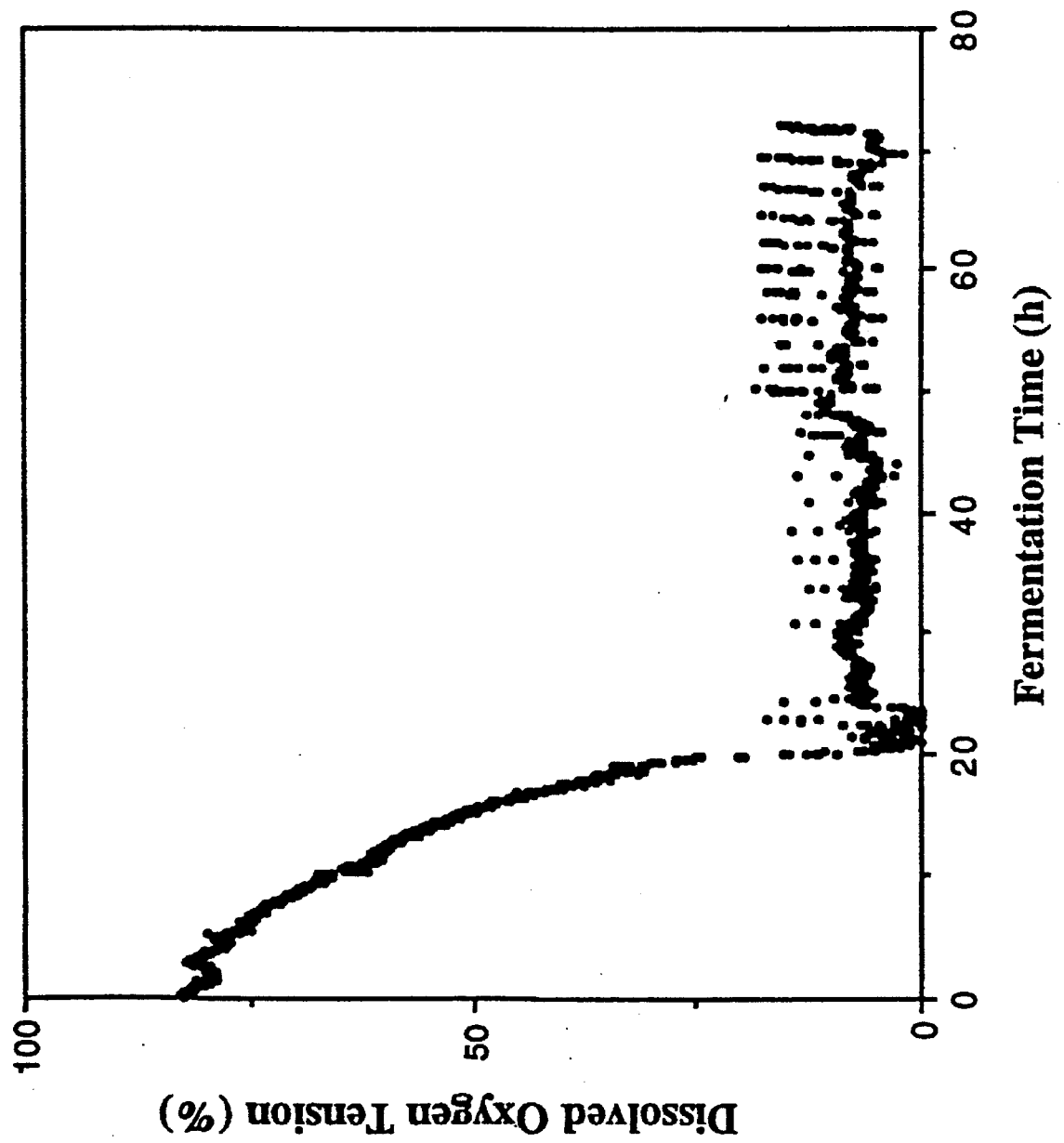
FIGS. 5A–5B Time-course data of a fed-batch culture with an agitation speed and an aeration rate switch.
Figure 5B:
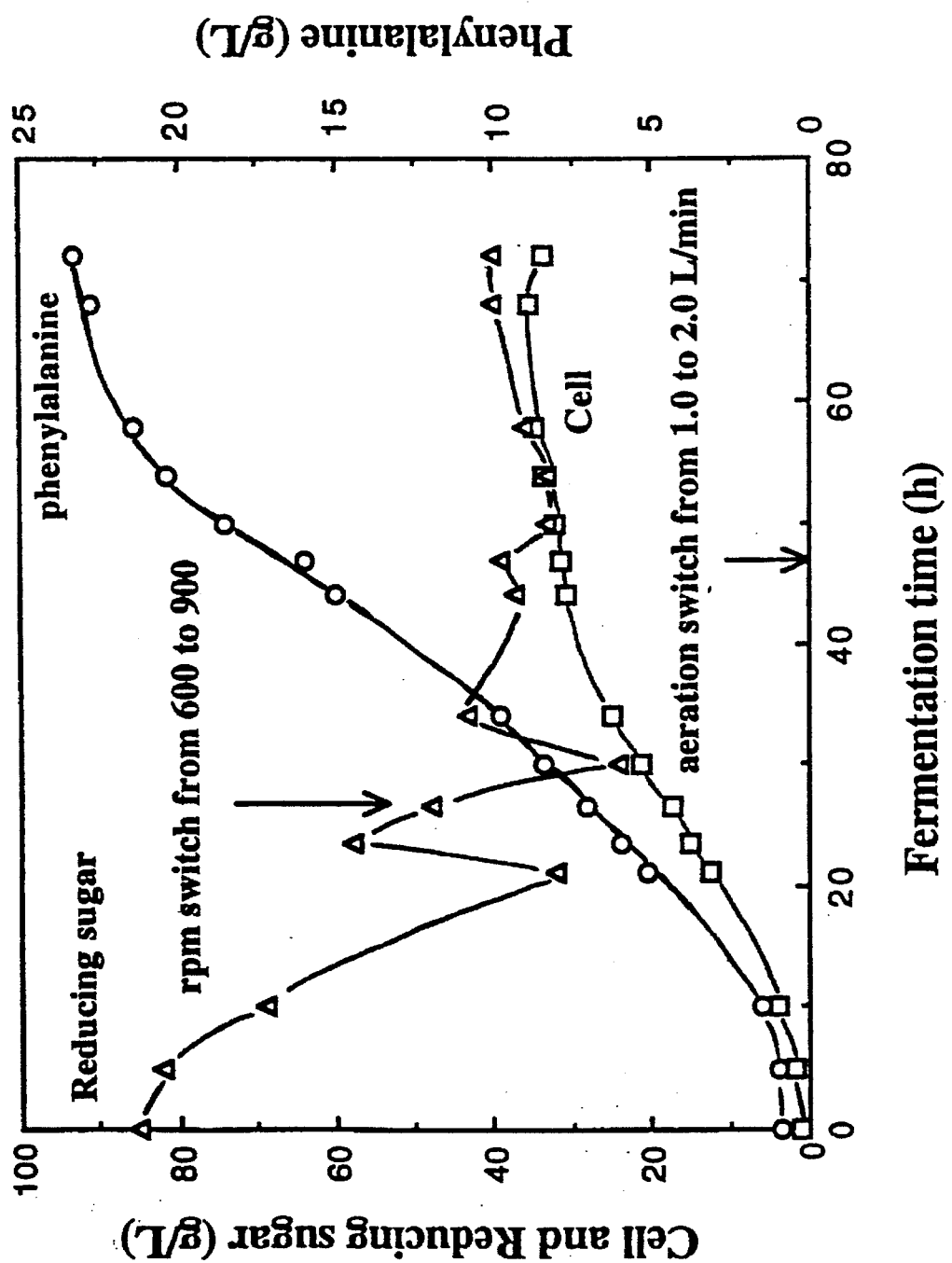

In order to reach phenylalanine concentration of 20 g/L, it took 77 hours for the run under a regular oxygen supply rate (FIG. 4A–4B), but it took only 54 hours for the run with increasing oxygen supply rate (FIGS. 5A–5b). That is, the fermentation time could be decreased by 23 hours.

We claim:

1. A process for L-phenylalanine production comprising the steps of fermenting *Corynebacterium glutamicum* within a fermentation medium and supplying oxygen to said fermentation medium, characterized by said oxygen being supplied with an increasing rate to decrease product feedback inhibition of phenylalanine as phenylalanine concentration increases.

2. The process for L-phenylalanine production according to claim 1, wherein said fermentation medium has a pH value in the range of 6.0 to 7.5.

3. The process for L-phenylalanine production according to claim 1, said process being operated in a temperature between 25° C. and 35° C.

* * * * *